United States Patent
Abu Dayyeh

(10) Patent No.: US 12,161,574 B2
(45) Date of Patent: Dec. 10, 2024

(54) METHODS AND DEVICES FOR GASTRICINTESTINAL TRACT BYPASS

(71) Applicant: Mayo Foundation for Medical Education and Research, Rochester, MN (US)

(72) Inventor: Barham K. Abu Dayyeh, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 403 days.

(21) Appl. No.: 16/901,965

(22) Filed: Jun. 15, 2020

(65) Prior Publication Data

US 2020/0390580 A1    Dec. 17, 2020

Related U.S. Application Data

(60) Provisional application No. 62/861,846, filed on Jun. 14, 2019.

(51) Int. Cl.
*A61F 5/00* (2006.01)
(52) U.S. Cl.
CPC .......... *A61F 5/0079* (2013.01); *A61F 5/003* (2013.01); *A61F 5/004* (2013.01)
(58) Field of Classification Search
CPC ...... A61F 5/003; A61F 5/0076; A61F 5/0079; A61B 17/1114
See application file for complete search history.

(56) References Cited

U.S. PATENT DOCUMENTS

| | | | |
|---|---|---|---|
| 7,803,195 B2 * | 9/2010 | Levy | A61F 5/0079 604/9 |
| 8,012,140 B1 | 9/2011 | Kagan et al. | |
| 8,678,994 B2 | 3/2014 | Sonnenschein et al. | |
| 8,911,393 B2 | 12/2014 | Levy et al. | |
| 10,292,854 B2 | 5/2019 | Abu Dayyeh | |
| 2002/0143387 A1 | 10/2002 | Soetikno et al. | |
| 2004/0039452 A1 | 2/2004 | Bessler | |
| 2004/0092892 A1 * | 5/2004 | Kagan | A61B 17/0401 604/270 |

(Continued)

FOREIGN PATENT DOCUMENTS

| | | |
|---|---|---|
| CA | 2997727 | 3/2017 |
| WO | WO 2006/014496 | 2/2006 |
| WO | WO 2019/009918 | * 1/2019 |

OTHER PUBLICATIONS

Abu Dayyeh et al., "Endoscopic sclerotherapy for the treatment of weight regain after Roux-en-Y gastric bypass: outcomes, complications, and predictors of response in 575 procedures," Gastrointest. Endoscopy, Aug. 2012, 76(2):275-282.

(Continued)

*Primary Examiner* — Elizabeth Houston
*Assistant Examiner* — Lindsey Bachman
(74) *Attorney, Agent, or Firm* — Fish & Richardson P.C.

(57) ABSTRACT

A system for bypassing a portion of a small intestine. The system includes an occlusion device and a bypass device. The occlusion device includes a tubular body, an occlusion member at a distal end portion of the tubular body, and an anchor member at a proximal end portion of the tubular body. The bypass device includes a liner, and an anchor member at a proximal end portion of the liner.

14 Claims, 10 Drawing Sheets

(56) References Cited

U.S. PATENT DOCUMENTS

| | | |
|---|---|---|
| 2006/0020247 A1 | 1/2006 | Kagan et al. |
| 2006/0036267 A1 | 2/2006 | Saadat et al. |
| 2006/0189845 A1 | 8/2006 | Maahs et al. |
| 2008/0243031 A1 | 10/2008 | Seibel et al. |
| 2009/0093837 A1 | 4/2009 | Dillon |
| 2011/0245752 A1 | 10/2011 | Levine et al. |
| 2011/0251555 A1 | 10/2011 | Ducharme et al. |
| 2011/0257580 A1 | 10/2011 | Meade et al. |
| 2012/0253259 A1 | 10/2012 | Belhe et al. |
| 2013/0079603 A1 | 3/2013 | Vargas |
| 2014/0236064 A1 | 8/2014 | Binmoeller et al. |
| 2017/0027729 A1 | 2/2017 | Dayyeh |
| 2017/0079822 A1* | 3/2017 | Farrugia .............. A61F 5/0013 |
| 2019/0298401 A1 | 10/2019 | Gupta et al. |
| 2019/0298559 A1* | 10/2019 | Gupta ................. A61B 17/1114 |
| 2022/0125434 A1 | 4/2022 | Abu Dayyeh |

OTHER PUBLICATIONS

Abu Dayyeh et al., "Endoscopic Sleeve Gastroplasty Alters Gastric Physiology and Induces Loss of Body Weight in Obese Individuals," Clin. Gastroenterol. Hepatology, Jan. 2017, 15(1):37-43.e1.

Abu Dayyeh et al., "Endoscopic sleeve gastroplasty: a potential endoscopic alternative to surgical sleeve gastrectomy for treatment of obesity," Gastrointest. Endoscopy, Sep. 2013, 78(3):530-535.

Abu Dayyeh et al., "Gastrojejunal stoma diameter predicts weight regain after Roux-en-Y gastric bypass," Clin. Gastroenterol. Hepatology, Mar. 2011, 9(3):228-233.

Almalki et al., "Laparoscopic gastric bypass for the treatment of type 2 diabetes: a comparison of Roux-en-Y versus single anastomosis gastric bypass," Surg. Obes. Relat. Diseases, Apr. 2018, 14(4):509-515.

Batterham et al., "Mechanisms of Diabetes Improvement Following Bariatric/Metabolic Surgery," Diabetes Care, Jun. 2016, 39(6):893-901.

Cummings et al., "Role of the bypassed proximal intestine in the anti-diabetic effects of bariatric surgery," Surg. Obes. Relat. Diseases, Mar. 2007, 3(2):109-115.

Dorman et al., "Case-matched outcomes in bariatric surgery for treatment of type 2 diabetes in the morbidly obese patient," Ann. Surgery, Feb. 2012, 255(2):287-293.

Frohnert et al., "Increased adipose protein carbonylation in human obesity," Obesity, Sep. 2011, 19(9):1735-1741.

Himpens et al., "4th IFSO Global Registry Report—2018," The IFSO Global Registry, Sep. 2018, 84 pages.

Ikramuddin et al., "Effect of reversible intermittent intraabdominal vagal nerve blockade on morbid obesity: the ReCharge randomized clinical trial," JAMA, Sep. 3, 2014, 312(9):915-922.

Ikramuddin et al., Lifestyle Intervention and Medical Management With vs Without Roux-en-Y Gastric Bypass and Control of Hemoglobin A1c, LDL Cholesterol, and Systolic Blood Pressure at 5 Years in the Diabetes Surgery Study, JAMA, Jan. 16, 2018, 319(3):266-278.

Ikramuddin et al., "Roux-en-Y gastric bypass vs intensive medical management for the control of type 2 diabetes, hypertension, and hyperlipidemia: the Diabetes Surgery Study randomized clinical trial," JAMA, Jun. 5, 2013, 309(21):2240-2249.

Jahansouz et al., "Antibiotic-induced disruption of intestinal microbiota contributes to failure of vertical sleeve gastrectomy," Ann. Surgery, Jun. 2019, 269(6):1092-1100.

Jahansouz et al., "Bile Acids Increase Independently From Hypocaloric Restriction After Bariatric Surgery," Ann. Surgery, Dec. 2016, 264(6):1022-1028.

Jahansouz et al., "Roux-en-Y Gastric Bypass Acutely Decreases Protein Carbonylation and Increases Expression of Mitochondrial Biogenesis Genes in Subcutaneous Adipose Tissue," Obes. Surgery, Dec. 2015, 25(12):2376-2385.

Jahansouz et al., "Sleeve gastrectomy drives persistent shifts in the gut microbiome," Surg. Obes. Relat. Diseases, Jun. 2017, 13(6):916-924.

Jirapinyo et al., "Evaluation of an endoscopic suturing device for transoral outlet reduction in patients with weight regain following Roux-en-Y gastric bypass," Endoscopy, Jul. 2013, 45(7):532-536.

Kumar et al., "Endoscopic sutured gastroplasty: procedure evolution from first-in-man cases through current technique," Surg. Endoscopy, Apr. 2018, 32(4):2159-2164.

Robert et al., "Efficacy and safety of one anastomosis gastric bypass versus Roux-en-Y gastric bypass for obesity (YOMEGA): a multicentre, randomised, open-label, non-inferiority trial," Lancet, Mar. 30, 2019, 393(10178):1299-1309.

Rubino et al., "The mechanism of diabetes control after gastrointestinal bypass surgery reveals a role of the proximal small intestine in the pathophysiology of type 2 diabetes," Ann. Surgery, Nov. 2006, 244(5):741-749.

Ryou et al., "ASGE Endo Vators Summit: Defining the role and value of endoscopic therapies in obesity management," Gastrointest. Endoscopy, Nov. 2017, 86(5):757-767.

The GBD 2015 Obesity Collaborators et al., "Health Effects of Overweight and Obesity in 195 Countries over 25 Years," N. Engl. J. Medicine, Jul. 6, 2017, 377(1):13-27.

Vargas et al., "Transoral outlet reduction with full thickness endoscopic suturing for weight regain after gastric bypass: a large multicenter international experience and meta-analysis," Surg. Endoscopy, Jan. 2018, 32(1):252-259.

Whitson et al., "Adipokine response in diabetics and nondiabetics following the Roux-en-Y gastric bypass: a preliminary study," J. Surg. Research, Oct. 2007, 142(2):295-300.

EP Extended Search Report in European Appln. No. 20744372.2, dated May 16, 2022, 12 pages.

EP Partial Supplementary Search Report in European Appln. No. 20744372.2, dated Feb. 15, 2022, 14 pages.

PCT International Preliminary Report on Patentability in International Appln. No. PCT/US2015/025370, mailed on Oct. 27, 2016, 7 pages.

PCT International Preliminary Report on Patentability in International Appln. No. PCT/US2020/014374, dated Jul. 27, 2021, 9 pages.

PCT International Search Report and Written Opinion in International Appln. No. PCT/US2020/014374, dated Mar. 25, 2020, 10 pages.

PCT International Search Report in International Appln. No. PCT/US2015/025370, mailed on Jul. 15, 2015, 15 pages.

Tierney et al., "Overtube use in gastrointestinal endoscopy," Gastrointest. Endosc., Nov. 2009, 70(5):828-834.

U.S. Appl. No. 15/303,333, filed Oct. 11, 2016, Barham K. Abu Dayyeh.

U.S. Appl. No. 17/424,024, filed Jul. 19, 2021, Barham K. Abu Dayyeh.

* cited by examiner

METHODS AND DEVICES FOR GASTRICINTESTINAL TRACT BYPASS

CROSS-REFERENCE TO RELATED APPLICATIONS

This application claims the benefit of U.S. Provisional Application Ser. No. 62/861,846, filed on Jun. 14, 2019. The disclosure of the prior application is considered part of (and is incorporated by reference in) the disclosure of this application.

BACKGROUND

1. Technical Field

This document relates to methods and materials for the medical treatment of conditions such as obesity and metabolic diseases. For example, this document relates to methods and devices for bypassing portions of the gastrointestinal tract to reduce weight and/or improve diabetes control.

2. Background Information

Obesity is a problem crossing age, ethnic, and socioeconomic boundaries. In general, obesity means having too much body fat. Morbid obesity is a serious health condition that can interfere with basic physical functions such as breathing or walking. Individuals who are morbidly obese are at greater risk for illnesses including diabetes, high blood pressure, sleep apnea, gastroesophageal reflux disease, infertility, low back pain, asthma, gallstones, osteoarthritis, heart disease, and cancer. Billions of dollars are spent each year treating millions of individuals around the world suffering from such diseases. Many people suffering from morbid obesity find it nearly impossible to lose weight by controlling their diet and exercising.

While obesity and metabolic disease have reach pandemic proportions, yet to date non-surgical treatment modalities focusing on life-style interventions or pharmacotherapies have failed to achieve sufficient weight loss or have weight independent impact on the metabolic consequences of obesity. Bariatric surgery has not only offered a select group of morbidly obese patients effective and durable weight loss, but has also ushered a better understanding of the role of gastrointestinal tract and regulating energy intake and metabolism through weight-loss dependent and independent pathways coning the term metabolic surgery that is applicable to metabolic disease, such as type II diabetes, independent from weight. It is now clear the bariatric surgery results in significant weight loss through the manipulation of multiple gastric and small intestinal pathways, yet the majority of its weight independent effect results from the bypass of the first 150 cm of the small intestines to allow mixing of pancreaticobiliary secretions with food in the distal jejunum. Given the poor penetrance and patient acceptance of bariatric and metabolic surgery, minimally invasive surgical and endoscopic options with improved safety, efficacy, and patient acceptance have been under intense development efforts.

The single Anastomosis Gastric Bypass, also known as "mini-gastric bypass" is a minimally invasive procedure performed with laparoscopic technique, where the surgeon first reduces the size of the "working" stomach by separating a tube-like pouch of stomach from the rest of the stomach. This tubular gastric pouch is then connected (anastomosed) to the intestine, bypassing up to 150 cm of the upper part of the intestine. This technique differs from the traditional Roux-en-Y Bypass (RYGB) which requires two connections (anastomoses), thus improved patient acceptance and safety. This technique is very effective for both weight loss and diabetes resolution, which typical weight loss ranging between 30% to 40% of body weight. Long-term data shows that this procedure results in higher weight loss and better resolution of diabetes than the traditional RYGB. The superior diabetes remission rate of this procedure is attributed to both the greater weight loss and the longer pancreaticobiliary limb length. Despite improved safety this is still an invasive surgery with poor patient acceptance and penetrance, and bile reflux through the single gastrojejunal anastomosis causing gastritis and esophagitis has been a major limitation of this approach.

SUMMARY

This document describes methods and materials for occluding and bypassing a portion of the gastrointestinal tract. For example, this document describes methods and devices for bypassing portions of the gastrointestinal (GI) tract which can result in decreased nutritional uptake, weight loss, and improvement in diabetes control and other metabolic disease such as non-alcoholic fatty liver disease.

In one aspect, this disclosure is directed to a system for bypassing a portion of a small intestine. The system includes an occlusion device configured to extend from an anastomosis between a stomach and the small intestine to a portion of the small intestine proximal the stomach and a bypass device configured to extend from the anastomosis through a portion of the small intestine. In some cases, the occlusion device can include an occlusion member configured to occlude the proximal portion of the small intestine. In some cases, the occlusion member can be an inflatable balloon. In some cases, the occlusion device can include an inflation line communicably coupled to the inflatable balloon. In some cases, the inflation line can be removably coupled to the occlusion device. In some cases, the occlusion member can be a bumper. In some cases, the bumper can include a soft pliable material. In some cases, the occlusion device can include an anchor member configured to reside in the anastomosis. In some cases, the anchor member can have a conical shape.

In some cases, the occlusion device can include a tubular body. In some cases, the tubular body can be tapered. In some cases, the tubular body can be flexible. In some cases, the tubular body can include a proximal opening. In some cases, the proximal opening can be configured to receive a portion of the bypass device. In some cases, the bypass device can include a liner and an anchor member. In some cases, the liner can be made of a flexible material. In some cases, the liner can have a length of about 40 cm to about 100 cm. In some cases, the anchor member can be configured to engage with an anchor member of the occlusion device. In some cases, the anchor member can have a conical shape. In some cases, the anchor member can include a locking member configured to engage with an anchor member of the occlusion device. In some cases, the locking member can extend at an angle from the anchor member.

In another aspect, this disclosure is directed to a system for bypassing a portion of a small intestine. The system includes an occlusion device and a bypass device. The occlusion device includes a tubular body, an occlusion member at a distal end portion of the tubular body, and an anchor member at a proximal end portion of the tubular body. The bypass device includes a liner and an anchor member at a proximal end portion of the liner.

In some cases, the occlusion device can be configured to extend from an anastomosis between a stomach and the small intestine to a portion of the small intestine proximal the stomach, and the bypass device can be configured to extend from the anastomosis through a portion of the small intestine. In some cases, the occlusion member can be configured to occlude the proximal portion of the small intestine. In some cases, the occlusion member can be an inflatable balloon. In some cases, the occlusion device can include an inflation line communicably coupled to the inflatable balloon. In some cases, the inflation line can be removably coupled to the occlusion device. In some cases, the occlusion member can be a bumper. In some cases, the bumper can include a soft pliable material.

In some cases, the anchor member can be configured to reside in an anastomosis between a stomach and a jejunum. In some cases, the anchor member of the occlusion device can be a conical shape. In some cases, the tubular body can be tapered. In some cases, the tubular body can be flexible. In some cases, the tubular body can include a proximal opening. In some cases, the proximal opening can be configured to receive a portion of the bypass device. In some cases, the liner can be made of a flexible material. In some cases, the liner can have a length of about 40 cm to about 100 cm. In some cases, the anchor member of the bypass device can be configured to engage with an anchor member of the occlusion device. In some cases, the anchor member of the bypass device can have a conical shape. In some cases, the anchor member of the bypass device can include a locking member configured to engage with an anchor member of the occlusion device. In some cases, the locking member can extend at an angle from the anchor member.

In yet another aspect, this disclosure is directed to a method of bypassing a portion of a small intestine. The method includes positioning an occlusion device between an anastomosis and a portion of the small intestine proximal a stomach, where the anastomosis is between the stomach and a distal portion of the small intestine and positioning a bypass device from the anastomosis through the distal portion of the small intestine. In some cases, the portion of the small intestine proximal the stomach can be a duodenum. In some cases, the portion of the small intestine proximal the stomach can be a pyloric sphincter. In some cases, the portion of the small intestine proximal the stomach can be a pyloric channel. In some cases, the portion of the small intestine proximal the stomach can be a gastric antrum. In some cases, positioning the occlusion device can include positioning an anchor member of the occlusion device in the anastomosis. In some cases, positioning the bypass device can include coupling an anchor member of the bypass device to the anchor member of the occlusion device. In some cases, positioning the occlusion device can include positioning an occlusion member of the occlusion device in the portion of the small intestine proximal the stomach. In some cases, the occlusion member can be an inflatable balloon, and the method can further include inflating the inflatable balloon. In some cases, the occlusion device can include a proximal opening, and positioning the bypass device can include passing a liner of the bypass device through the proximal opening of the occlusion device.

In another aspect, this disclosure is directed to a system for bypassing a portion of a small intestine. The system includes an occlusion device configured to extend from the esophagus, through a lower esophageal sphincter, to an anastomosis located between a stomach and the small intestine; and a bypass device configured to extend from the anastomosis through a portion of the small intestine. In some cases, the occlusion device extends across the stomach.

In another aspect, this disclosure is directed to a system for bypassing a portion of a small intestine. The system includes an occlusion device including a tubular body; an occlusion member disposed between a proximal portion and a distal portion of the tubular body; and an anchor member at a distal end portion of the tubular body. the system includes a bypass device including a liner; and an anchor member at a proximal end portion of the liner. In some cases, the occlusion member is a bumper. In some cases, the occlusion member has an inverted funnel shape.

In yet another aspect, this disclosure is directed to a method of bypassing a proximal portion of a small intestine. The method includes positioning an occlusion device between the esophagus and an anastomosis located between a stomach and a distal portion of the small intestine; and positioning a bypass device from the anastomosis through the distal portion of the small intestine. In some cases, the occlusion device extends from the esophagus, through a lower esophageal sphincter, across the stomach, and to the anastomosis. In some cases, the distal portion of the small intestine is the jejunum. In some cases, the proximal portion of the small intestine is the duodenum. In some cases, the method further includes positioning an occlusion member of the occlusion device at a lower esophageal sphincter, the occlusion member configured to prevent or reduce passage of a fluid or solid matter from the esophagus to the stomach. In some cases, the method further includes anchoring the occlusion device to the bypass device.

Particular embodiments of the subject matter described in this document can be implemented to realize one or more of the following advantages. In some embodiments, the devices and methods provided herein can cause weight loss and improvement in diabetes and other metabolic disease by, among other potential mechanisms, reducing the caloric intake and absorption of an individual. The methods for implanting the devices can be performed endoscopically, thus avoiding the need for the more invasive open or laparoscopic surgical procedures. The endoscopic technique for implanting the device can provide total direct visualization and stabilization of the GI tract anatomy in which the devices are implanted and can bypass longer segments of the GI tract given utilization of deep enteroscopy techniques and distal release of the device. In some embodiments, each of the proximal and distal ends of the occlusion device are anchored in relation to the GI tract to definitively position the device and to provide effective migration resistance. In some embodiments, a proximal end of the bypass device is anchored in relation to the GI tract to provide effective migration resistance.

Unless otherwise defined, all technical and scientific terms used herein have the same meaning as commonly understood by one of ordinary skill in the art to which this disclosure pertains. Although methods and materials similar or equivalent to those described herein can be used to practice the various embodiments, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the disclosure are set forth in the accompanying drawings and the description below. Other features, objects, and advantages of the methods and devices described will be apparent from the description, drawings, and from the claims.

DESCRIPTION OF DRAWINGS

Like reference numbers represent corresponding parts throughout.

DETAILED DESCRIPTION

This document relates to devices and methods for the medical treatment of conditions such as obesity and metabolic diseases. For example, this document provides methods and devices for bypassing portions of the GI tract to reduce nutritional update, decrease weight, and/or improve diabetes control.

Figure 1:
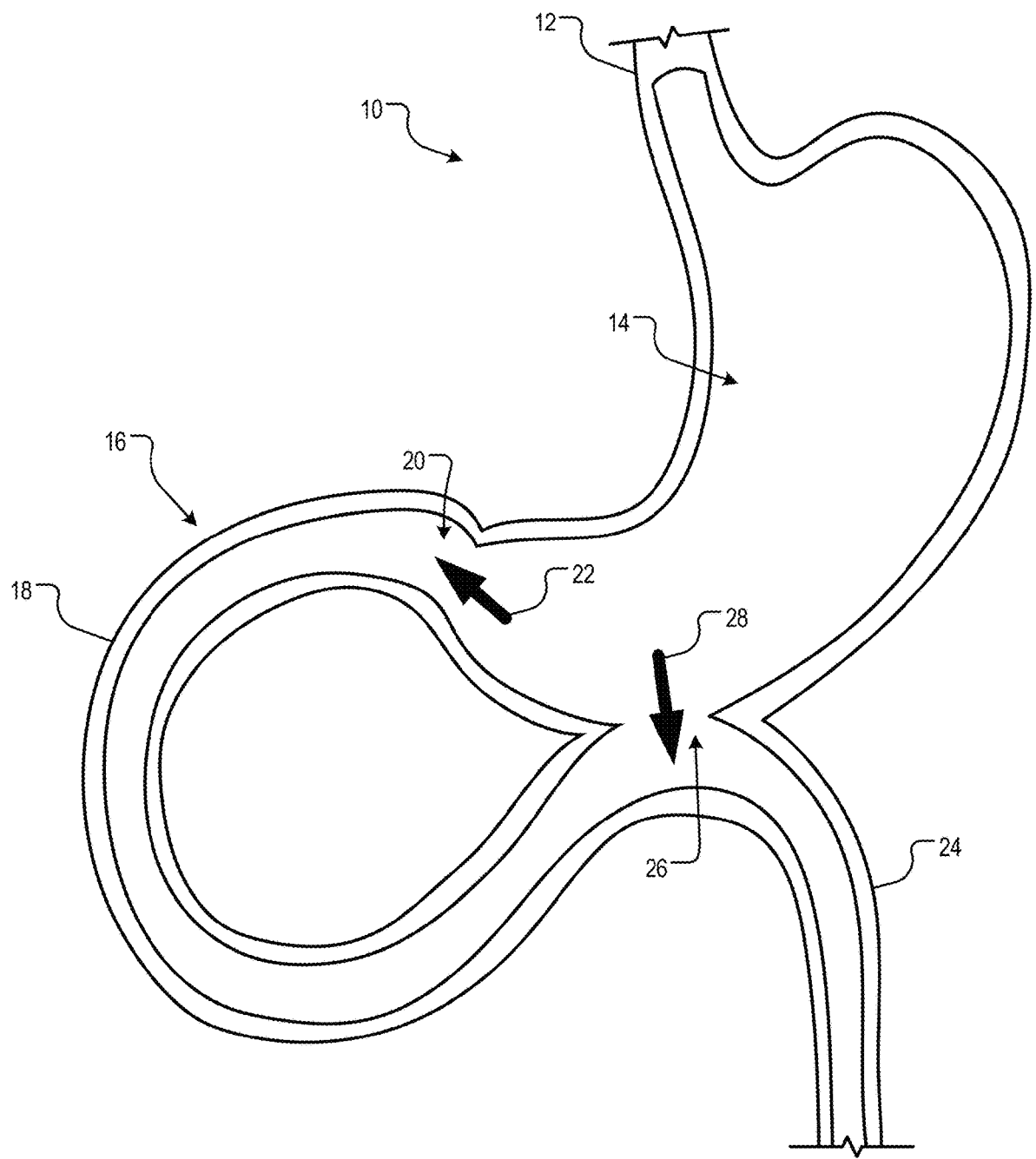
FIG. 1 is a diagram of an anastomosis between a stomach and a portion of an intestine, in accordance with some embodiments provided herein.

Referring to FIG. 1, a digestive tract 10 of a human can include an esophagus 12, a stomach 14, and a small intestine 16. The esophagus 12 connects the mouth to the stomach 14 and passes food to the stomach 14. The stomach 14 secretes digestive enzymes and gastric acid to aid in food digestion. The small intestine 16 is the organ where most of the absorption of nutrients and minerals from food takes place. The small intestine 16 includes a duodenum 18, a jejunum 24, and an ileum (not shown). A pyloric sphincter 20 controls a passage for movement 22 of partially digested food from the stomach 14 into the duodenum 18, which is about 25-38 cm long. Food then passes to the jejunum 24, which is about 2.25-2.75 m long. An anastomosis 26 can be created between the stomach 14 and the jejunum 24. Anastomosis 26 can created by a gastrojejunostomy. Anastomosis 26 can allow for movement 28 of food from the stomach 14 directly to the jejunum 24, bypassing the duodenum 18. In some cases, anastomosis 26 can include a stent, staples, magnets, balloons, or other means for maintaining the opening and connection between the stomach 14 and the jejunum 24. In some cases, anastomosis 26 can be about 1-4 cm in diameter.

Figure 2:
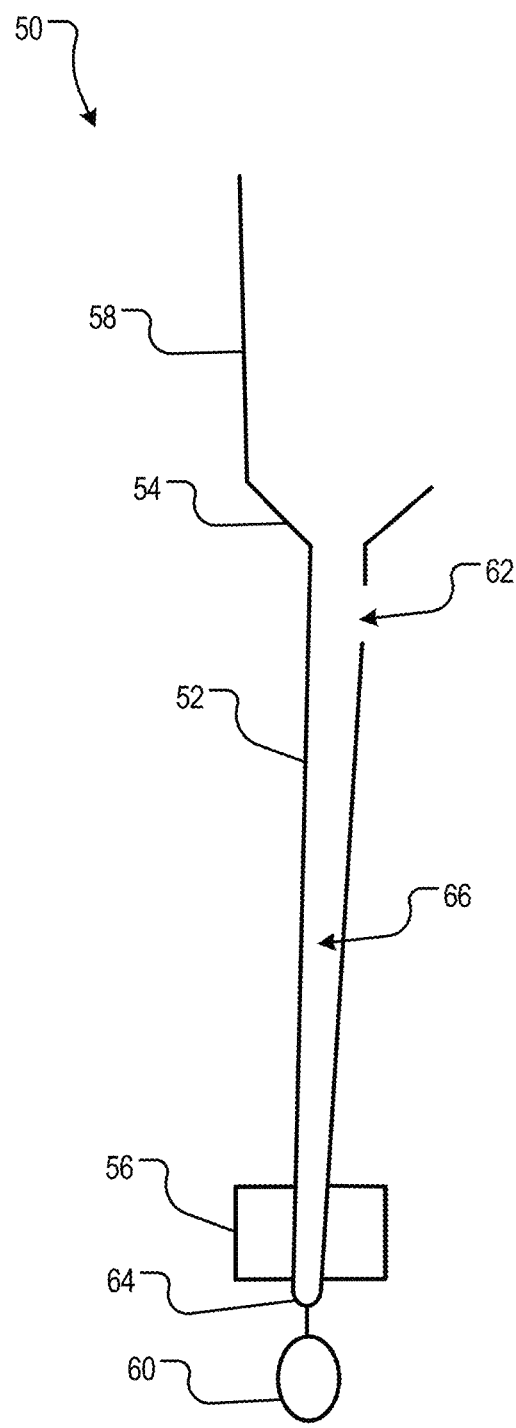
FIG. 2 is a cross sectional view of a occlusion device, in accordance with some embodiments provided herein.

Referring to FIG. 2, an occlusion device 50 can include a tubular body 52 and an occlusion member 56.

Tubular body 52 can be configured to extend from anastomosis 26 to the pyloric sphincter 20. In some cases, tubular body 52 can be tapered. For example, tubular member 52 can taper from a proximal end positioned near anastomosis 26 to a distal end positioned near the pyloric sphincter 20. In some cases, tubular body 52 can be flexible. For example, tubular body 52 can be made of a polymer (e.g., polyethylene) or a braided metal (such as nitinol) covered with silicon. In some cases, tubular member 52 can be hollow, creating an internal lumen 66. In some cases, a distal tip 64 of tubular member 52 may be occluded to prevent movement of fluid into and out of tubular member 52 at distal tip 64. In some cases, distal tip 64 can be configured to allow passage of a wire, but seal upon removal of the wire. In some cases, the aperture to allow passage of the wire is sized such that an insignificant amount of liquid could enter through the aperture.

In some cases, occlusion device 50 can include an anchor member 54. Anchor member 54 can be at a proximal end of the tubular member 52. Anchor member 54 can be configured to secure occlusion device 50 in place. In some cases, anchor member 54 can anchor occlusion device 50 in anastomosis 26 at a proximal end of occlusion device 50. In some cases, a portion of anchor member 54 is located in the stomach 14 and another portion of anchor member 54 is located in the jejunum 24 or the duodenum 18. In some cases, anchor member 54 can be conically shaped as anchor member 54 extends away from tubular member 52. The conical shape can reduce the likelihood that all of anchor member 54 passes through anastomosis 26. In some cases, anchor member 54 can be configured to engage a stent that is located in anastomosis 26 and lock anchor member 54 into the stent. In some cases, anchor member 54 can be hollow and have an internal lumen that aligns with the internal lumen of the tubular member 52.

In some cases, tubular body 52 can include a proximal opening 62. Proximal opening 62 can be an aperture through one side of the tubular body 52. In some cases, proximal opening can be proximal the anchor member 54. Proximal opening 62 can be configured to allow passage of bypass device. In some cases, tubular member 52 can be positioned to align with the jejunum 24. The proximal opening 62 can provide access to the jejunum 24 from the stomach 14.

Occlusion member 56 can be positioned on a distal portion of tubular member 52. Occlusion member 56 can be configured to occlude the pyloric sphincter 20. In some cases, occlusion member 56 can be an inflatable balloon. In some cases, the inflatable balloon can be made of a soft conforming material. In some cases, the inflatable balloon can be inflated with a liquid or a gas. In some cases, the inflatable balloon can be inflated to a diameter from about 4 cm to about 6 cm. In some cases, occlusion device 50 can include an inflation line 58. Inflation line 58 can provide passage of a fluid from a device external to the patient to the inflatable balloon. In some cases, inflation line 58 can be disconnected from the tubular member 52 after inflation. In some cases, inflation line 58 can be disconnected from the anchor member 54. In some cases, occlusion member 56 can be a bumper. In some cases, occlusion member 56 can be a funnel that is delivered over an endoscope in a restrained position and assumes a funnel position once in the antrum with withdrawal of the endoscope. For example, the bumper can be made of a solid pliable material. In some cases, the bumper can be made of silicone or braided nitinol metal covered with silicon.

In some cases, occlusion device 50 can include a delivery loop 60. In some cases, delivery loop 60 can extend from the distal tip 64 of the tubular member 52. In some cases, delivery loop 60 can be removable. In some cases, delivery loop 60 can be configured to aid in delivery, positioning, and removal of the occlusion device 50.

Figure 3:
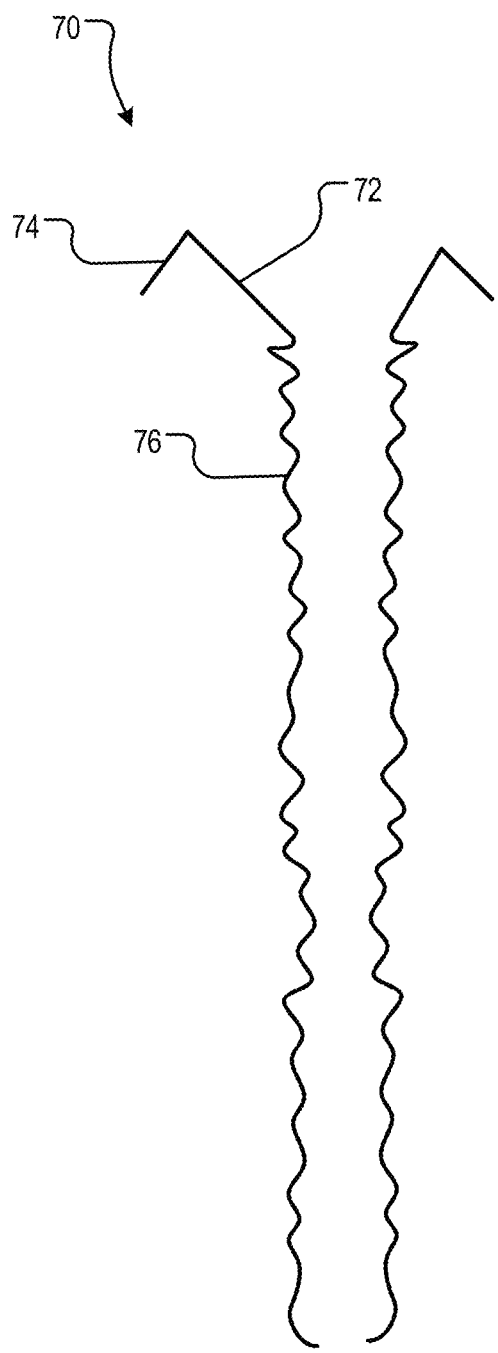
FIG. 3 is a cross sectional view of a bypass device, in accordance with some embodiments provided herein.

Referring to FIG. 3, a bypass device 70 can include an anchor member 72 and a liner 76.

Anchor member 72 can be configured to engage with the anchor member 54 of the occlusion device 50. Anchor member 72 can be at a proximal end portion of the liner 76. Anchor member 54 can be configured to secure bypass device 70 in place. In some cases, a portion of anchor member 72 can be located in the stomach 14 and another portion of anchor member 72 can be located in the jejunum 24 or the duodenum 18. In some cases, anchor member 54 can be conically shaped as anchor member 72 extends away from liner 76. The conical shape can be substantially similar to that of anchor member 54. In some cases, anchor member 72 can be slightly smaller than anchor member 54, such that anchor member 72 can reside in anchor member 54. In some cases, anchor member 54 can be hollow and have an internal lumen that aligns with an internal lumen of the liner 76.

In some cases, anchor member 72 can include a locking member 74. Locking member 74 can engage with anchor member 54. In some cases, locking member 74 can extend in an opposite direction from anchor member 72, creating a bend that sits over anchor member 54. In some cases, locking member 74 can be twisted to engage with anchor member 54 of the occlusion device 50. In some cases, locking member 74 can create an interference fit with anchor member 54 to engage with occlusion device 50.

Liner 76 can be configured to extend from anastomosis 26 through a portion of the jejunum 24. In some cases, liner 76 can be configured to cause the portion of the jejunum to be bypassed. For example, liner 76 can prevent the jejunum 24 from intaking nutrients passing through the liner 76. In some cases, liner 76 can extend through the proximal opening 62 of the occlusion device 50. In some cases, liner 76 can be made of a flexible material. For example, liner 76 can be made of Teflon. In some cases, liner 76 has a length of about 40 to about 100 cm.

Figure 4:
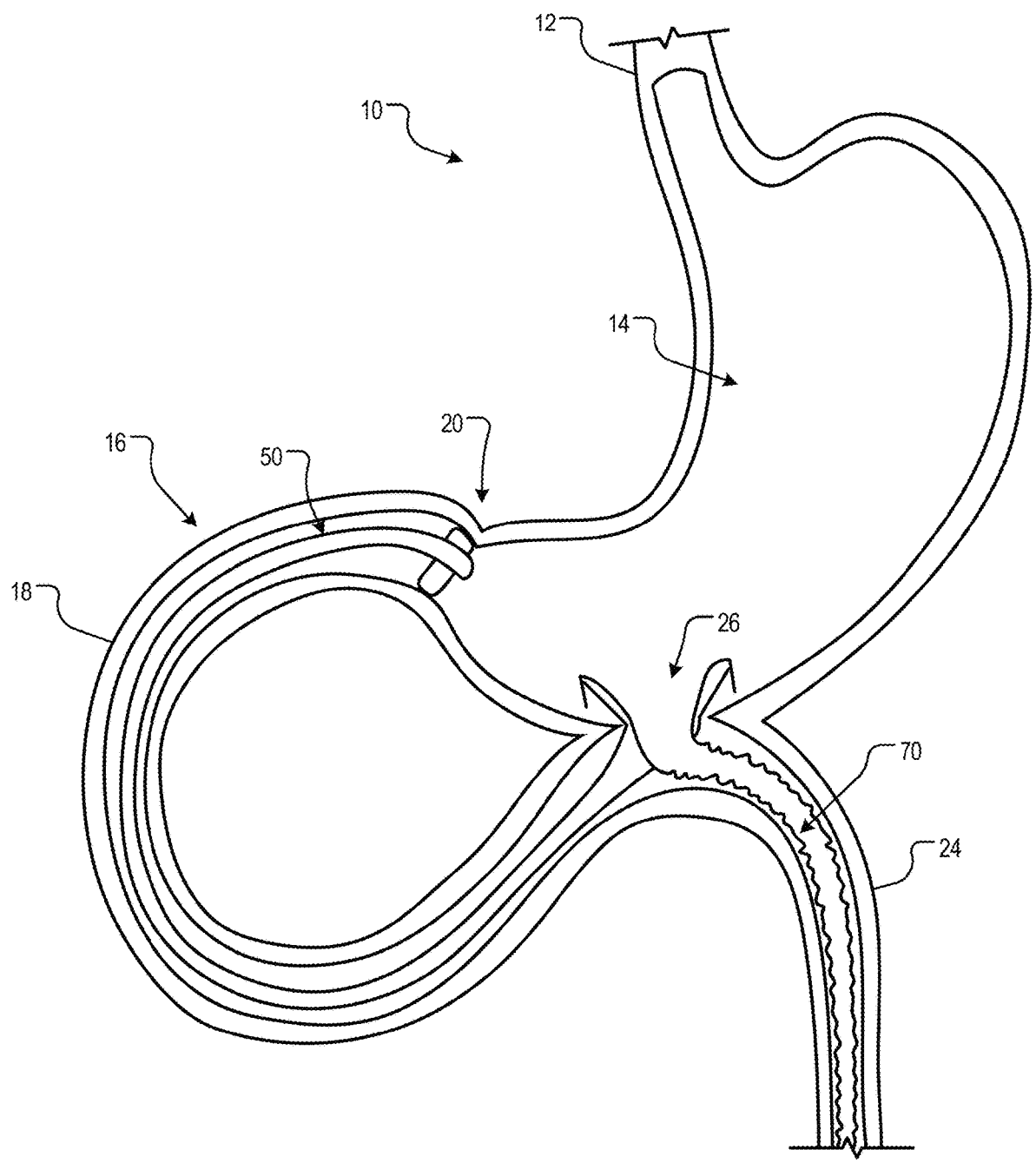
FIG. 4 is a schematic of the occlusion device of FIG. 2 and the bypass device of FIG. 3 implanted in the stomach and intestine, in accordance with some embodiments provided herein.

Referring to FIG. 4, the occlusion device 50 and the bypass device 70 can be implanted in the stomach 14 and small intestine 16. Delivery of the occlusion device 50 and the bypass device 70 can be performed using endoscopic techniques.

For example, once anastomosis 26 is created, a wire can be passed through the anastomosis 26 to the duodenum 18 and out the pyloric sphincter 20. In some cases, both ends of the wire extend out of the patients mouth. The occlusion device 50 can be passed over the wire until the occlusion member 56 is positioned proximal the pyloric sphincter 20 and the anchor member 54 is positioned at anastomosis 26. In some cases, the occlusion member 56 can be positioned in the gastric antrum, proximal to the pyloric channel. In some cases, once the occlusion device 50 is positioned, occlusion member 56 can be inflated (i.e., when occlusion member 56 is an inflatable balloon). In some cases, the inflatable balloon can be inflated to a diameter of about 4-6 cm. In some cases, inflation line 58 can be removed once the inflatable balloon has been inflated.

Once the occlusion device 50 is positioned, the bypass device 70 can be implanted. In some cases, a gastroscope can be advanced through anastomosis 26 and through the proximal opening 62 of the occlusion device 50. In some cases, after the gastroscope is advanced into the jejunum 24, a wire can be delivered through the gastroscope. In some cases, the bypass device 70 can be delivered over the wire into the jejunum 24. In some cases, the bypass device 70 can be secured to the occlusion device 50 by securing anchor member 72 of the bypass device 70 to anchor member 54 of the occlusion device 50. For example, the locking member 74 can secure anchor member 72 to anchor member 54.

The implantation of the occlusion device 50 and the bypass device 70 can occlude the pyloric sphincter 20 and redirect food directly to the jejunum 24. In some cases, the occlusion device 50 and bypass device 70 can maintain drainage of the bile and pancreas ducts through the papilla and diverting food away from the duodenum 18 and jejunum 24 with mixing of bile and pancreas secretion with nutrients in a mid or distal portion of the jejunum 24. In some cases, the occlusion device 50 and bypass device 70 can cause food to bypass about 60 to 150 cm of the small intestine 16.

Figure 5:
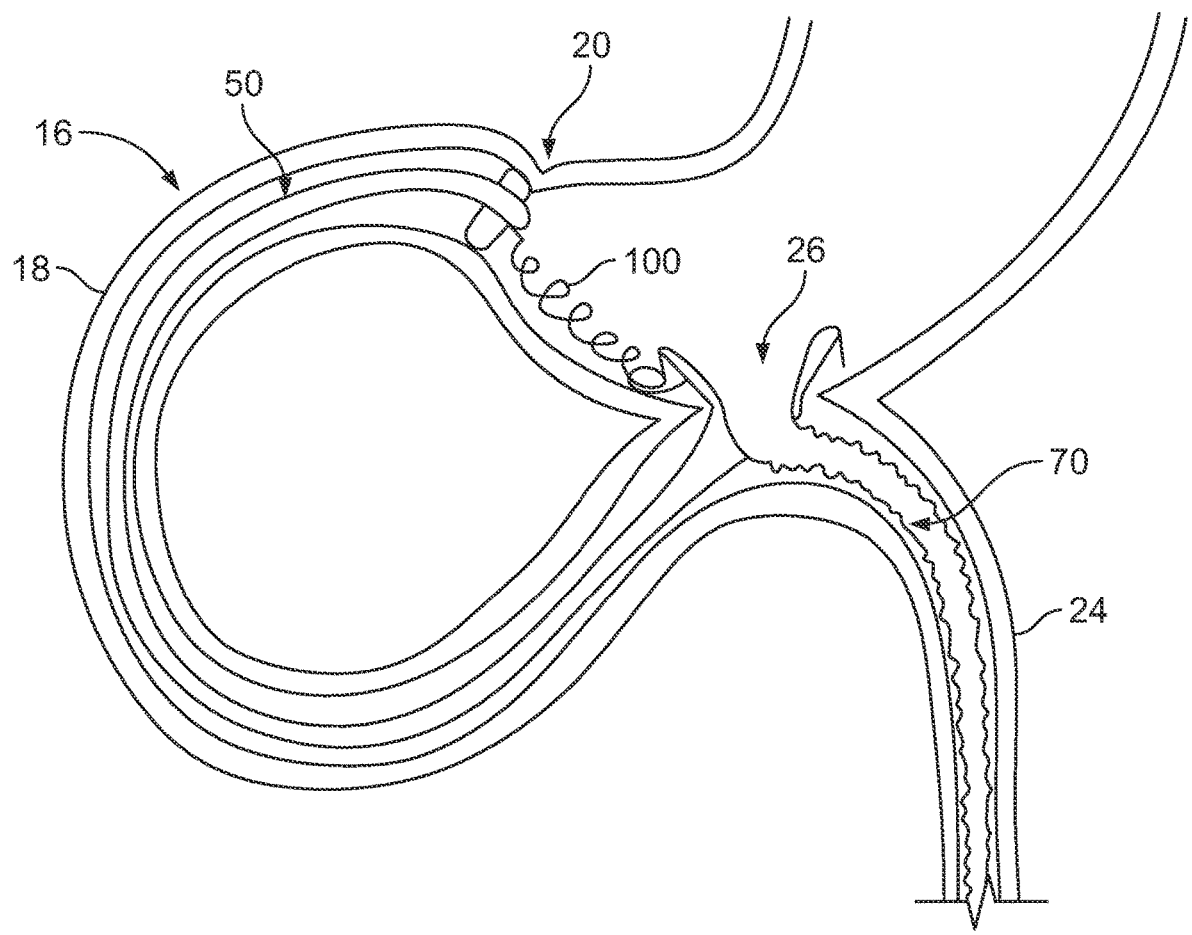
FIG. 5 is a schematic of the occlusion device of FIG. 2 and the bypass device of FIG. 3 connected via an expandable coil, in accordance with some embodiments provided herein.

Referring to FIG. 5, the occlusion device 50 can include an expandable coil 100 that secures the occlusion device 50 to the bypass device 70 on the gastric side of the apparatus. Connecting both devices can prevent migration or unnecessary movement of the occlusion device 50 or the bypass device 70 within the small intestine and/or the stomach. In some cases, the occlusion device 50 can include hooks that connect to the bypass device 70.

Figure 6:
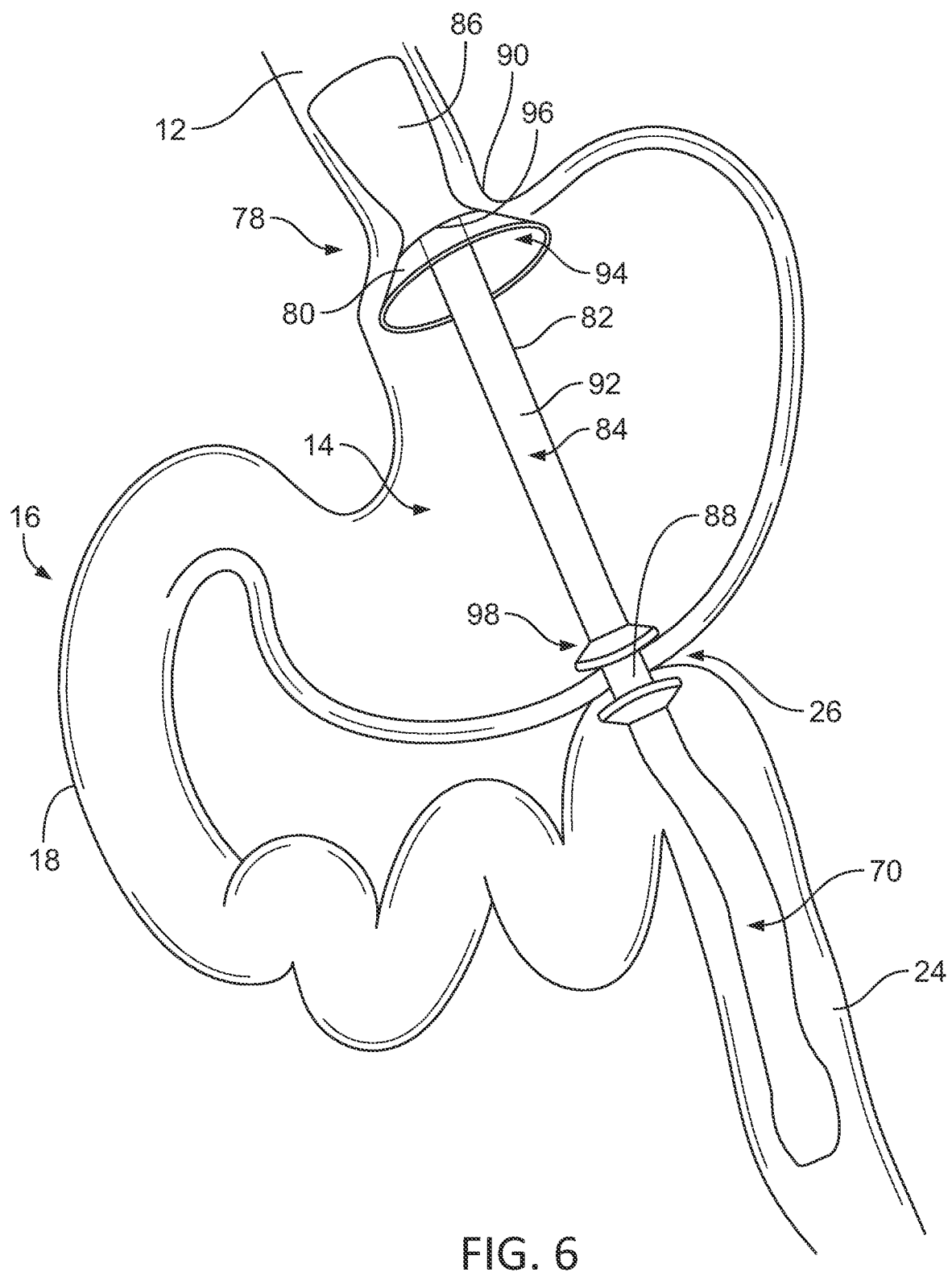
FIG. 6 is a schematic of an example esophageal and stomach bypass device of FIG. 3, in accordance with some embodiments provided herein.

Referring to FIG. 6, an esophageal occlusion device 78 and the bypass device 70 can be implanted in the stomach 14 and small intestine 16. The esophageal occlusion device 78 can have a tubular body 82, an occlusion member 80, and an anchor member 88.

The tubular body 82 has a proximal portion 86 and a distal portion 92. Proximal portion 86 can be configured to extend from the esophagus 12 to the lower esophageal sphincter 90, which is a region of smooth muscle thickening at the esophagogastric junction. In some cases, the proximal portion 86 can be tapered. For example, proximal portion 86 can taper from a proximal section of the esophagus 12 to a distal end positioned near or at the lower esophageal sphincter 90. In some cases, proximal portion 86 can be flexible. For example, proximal portion 86 can be made of a polymer (e.g., silicone) Distal portion 92 can be configured to extend from the lower esophageal sphincter 90 to the anastomosis 26, extending across the internal space of the stomach 14. In some cases, the distal portion 92 can be tapered. For example, proximal portion 86 can taper from the lower esophageal sphincter 90 to near or at the anastomosis 26. In some embodiments, distal portion 92 is straight (i.e., not tapered). In some cases, distal portion 92 can be flexible. For example, distal portion 92 can be made of a polymer (e.g., silicone) or composite materials (e.g., nitinol covered with silicone). Tubular body 82 is hollow, thereby defining an internal lumen 84. Internal lumen 84 extends from the proximal portion 86 to the distal portion 92. In other words, proximal portion 86 and distal portion 92 share the same internal lumen 84.

The lower esophageal sphincter 90 may be occluded with occlusion member 80 to prevent ingested food and/or ingested fluid in the esophagus 12 from entering stomach 14 and to prevent movement of fluid (e.g., gastric fluid and/or ingested fluid) and/or ingested food from stomach 14 into esophagus 12. Occlusion member 80 can be positioned at or near the lower esophageal sphincter 90, in between the proximal portion 86 and the distal portion 92 of the esophageal occlusion device 78. Occlusion member 80 can be configured to occlude the lower esophageal sphincter 90. Occlusion member can have an inverted funnel shape having a wide base 94 and a narrow neck 96. In some cases, occlusion member 80 can be a bumper. In some cases, occlusion member 80 can be an inverted funnel that is delivered over an endoscope in a restrained position and assumes an inverted funnel position once in the cardia with withdrawal of the endoscope. For example, the bumper can be made of a solid pliable material (e.g., nitinol or nitinol coated with silicone). In some cases, occlusion member 80 can be an inflatable balloon. In some cases, the inflatable balloon can be made of a soft conforming material. In some cases, the inflatable balloon can be inflated with a liquid or a gas. In some cases, the inflatable balloon can be inflated to a diameter from about 30 cm to about 60 cm. In some cases, esophageal occlusion device 78 can include an inflation line. The inflation line can provide passage of a fluid from a device external to the patient to the inflatable balloon. In some cases, the inflation line can be disconnected from the tubular body 82 after inflation.

Anchor member 88 can be at a distal end of the distal portion 92 of the esophageal occlusion device 78. Anchor member 88 can be configured to secure esophageal occlusion device 78 in place. In some cases, anchor member 88 can anchor esophageal occlusion device 78 in anastomosis 26 at a distal end of esophageal occlusion device 78. In some cases, a portion of anchor member 88 is located in the stomach 14 and another portion of anchor member 88 is located in the jejunum 24. In some embodiments, a portion of anchor member 88 is located in the stomach 14 and another portion of anchor member 88 is located in the duodenum 18. In some cases, anchor member 88 can be conically shaped as anchor member 88 extends away from tubular body 82. The conical shape can reduce the likelihood that all of anchor member 88 passes through anastomosis 26. In some cases, anchor member 88 can be configured to engage a bypass device 70 that is located in anastomosis 26 and lock anchor member 88 into the bypass device 70. In some cases, anchor member 88 can be configured to engage an anchor member of bypass device 70 at a proximal end portion of a liner 76 of bypass device 70. In some cases, anchor member 88 can be hollow and have an internal lumen that aligns with the internal lumen 84 of the tubular body 82 and with the internal lumen of bypass device 70.

In some cases, tubular body 82 can include a distal opening 98. Distal opening 98 can be an aperture through one side of the tubular body 82. In some cases, distal opening 98 can be proximal to the anchor member 88. Distal opening 98 can be configured to be fluidically connected to bypass device 70, thereby allowing passage of fluid and/or solids from the tubular body 82, through the anchor member 88, and into the bypass device 70. In some cases, tubular body 82 can be positioned to align with the jejunum 24. The distal opening 98 can provide access to the jejunum 24 from the stomach 14.

Delivery of the esophageal occlusion device 78 and the bypass device 70 can be performed using endoscopic techniques. For example, once anastomosis 26 is created, a wire can be passed through the lower esophageal sphincter 90, through the gastrojejunal or gastroduodenal anastomosis into the duodenum and out of the subject mouth to create a pulley system. The wire can be used to articulate on a delivery shuttle system of the esophageal occlusion device 78. The delivery shuttle system has the bypass device 70 collapsed around it and can be pulled in place using traction and/or counter-traction applied to the wire externally. Once across the appropriate anatomy the bypass device 70 is detached from the shuttle system and expanded in place.

The implantation of the esophageal occlusion device 78 and the bypass device 70 can occlude the lower esophageal sphincter 78 and redirect food directly to the jejunum 24, thereby bypassing the stomach 14 and the duodenum 18. In some cases, the esophageal occlusion device 78 and bypass device 70 can cause food to bypass about 20 to 150 cm of the small intestine 16.

Figure 7:
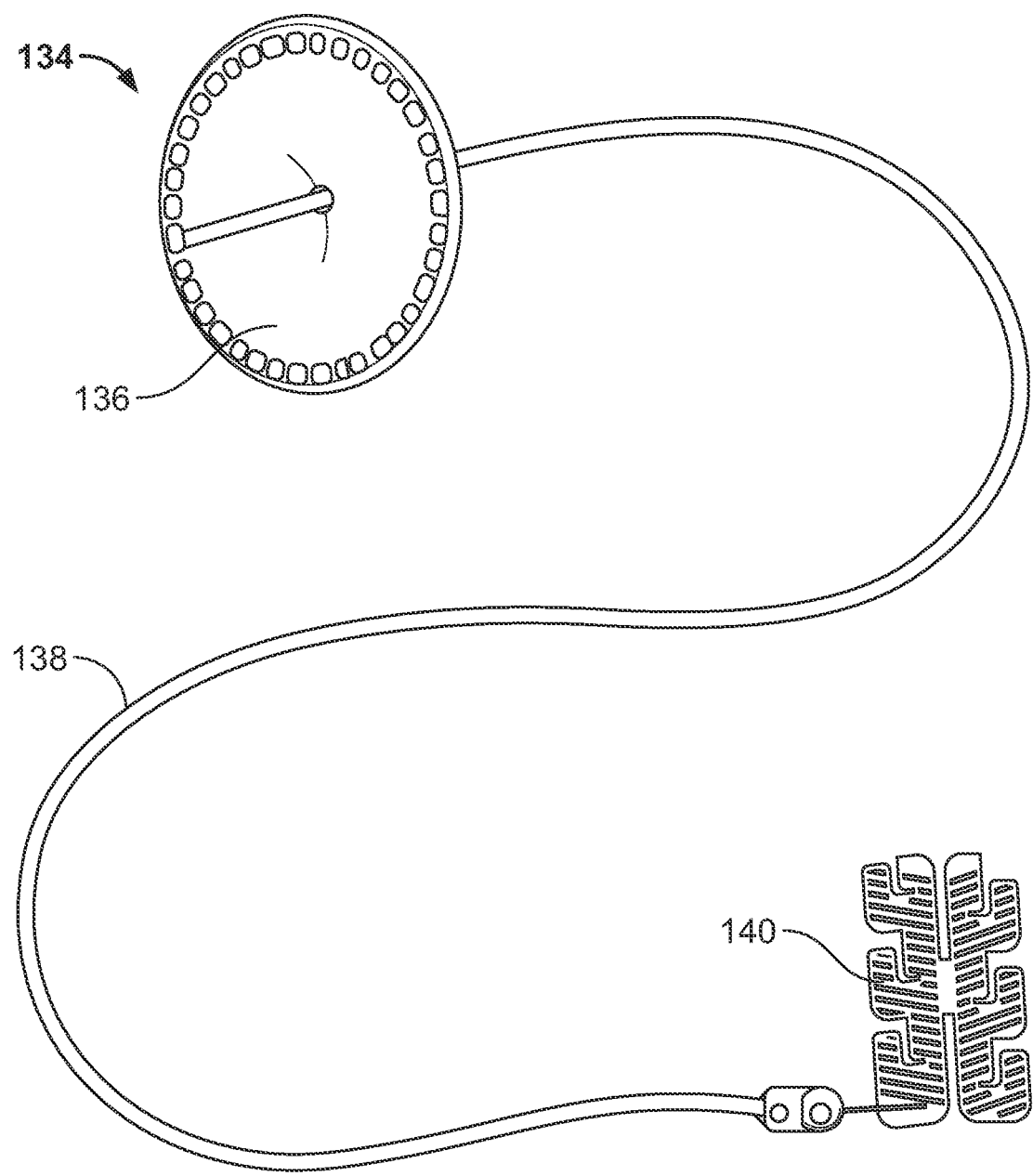
FIG. 7 is a side, perspective view of the example small intestinal occlusion device, in accordance with some embodiments provided herein.
Figure 8:
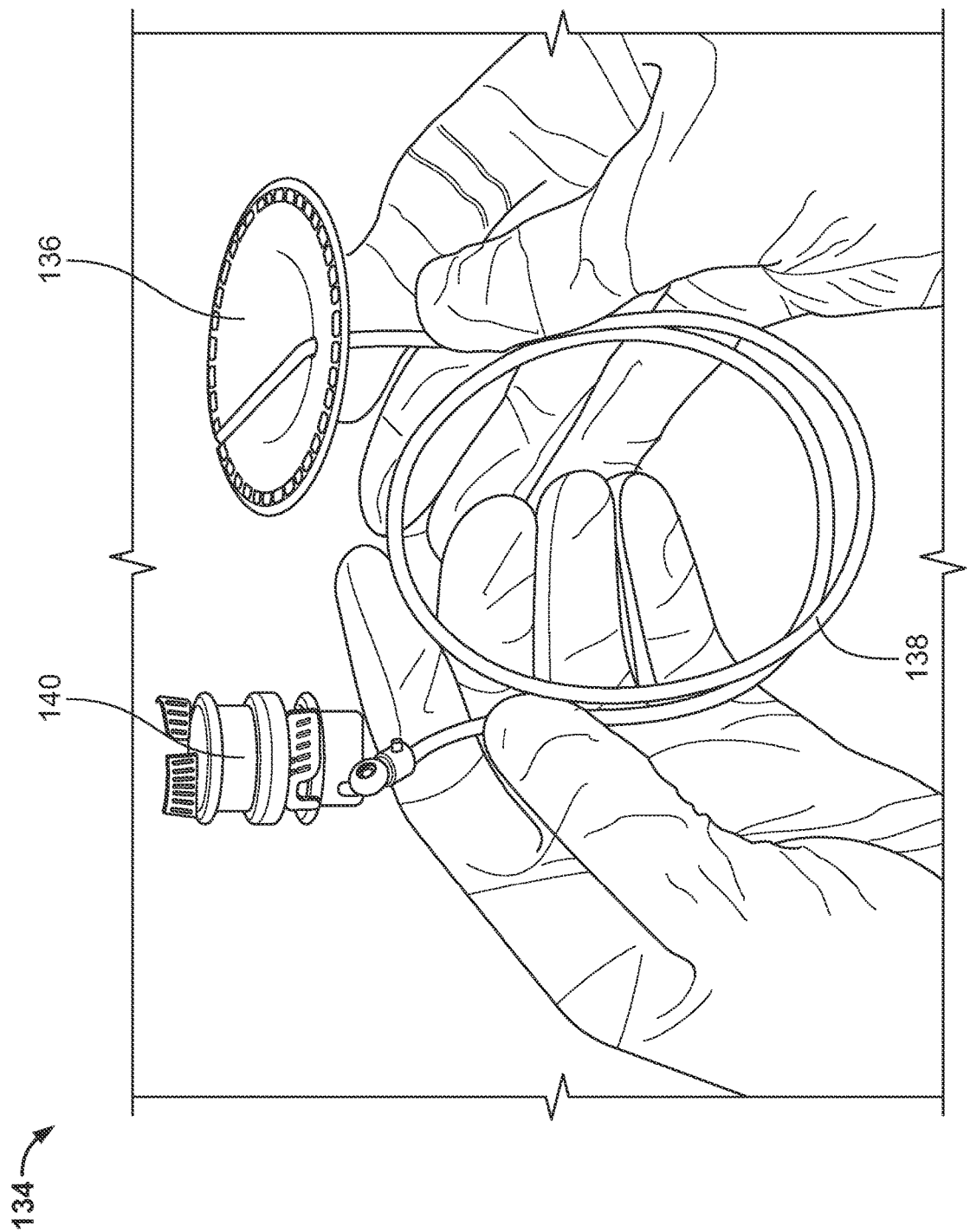
FIG. 8 is a side view of the example the small intestinal occlusion device of FIG. 7 with its tubular body in a coiled position, in accordance with some embodiments provided herein.

Referring to FIG. 7, a small intestinal occlusion device 134 includes an anchor member 140 at one end, an occlusion member 136 at an opposite end, and a tubular body 138 extending therebetween. The anchor member 140 can include an outer sleeve that encompasses a stent. The anchor member 140 can be configured to occlude the pyloric sphincter or pylorus between the stomach and the duodenum. The occlusion member 136 can have a substantially conical shape. In some cases, the occlusion member 136 is an expandable cone. In some cases, the occlusion member 136 is an expandable disk. The occlusion member 136 can be configured occlude or be placed within the anastomosis extending across a distal surface of the stomach and a proximal surface of the jejunum. Tubular body 138 can be flexible and is amenable to be in extended and coiled positions. FIG. 8 shows the small intestinal occlusion device 134 having its tubular body 138 in a coiled position.

Figure 9:
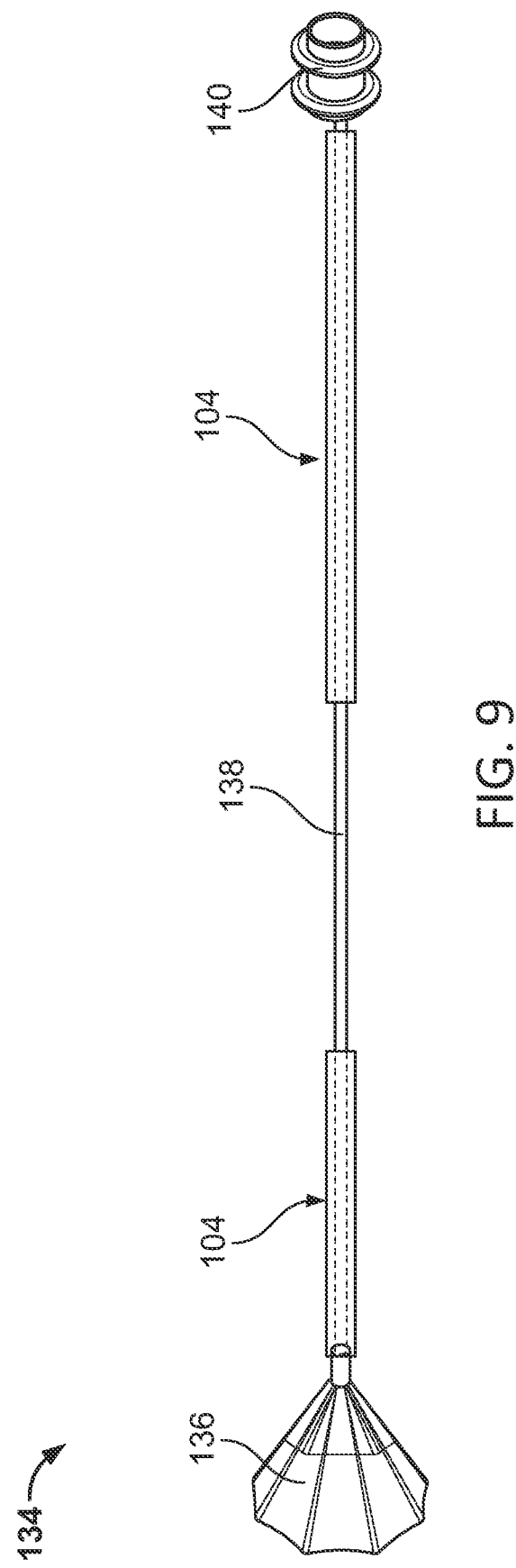
FIG. 9 is a side view of the example of the small intestinal occlusion device of FIG. 7 with its tubular body in a stretched position, in accordance with some embodiments provided herein.

FIG. 9 shows the small intestinal occlusion device 134 having its tubular body 138 in an extended position. Tubular body 138 can include stretchable areas 104 along its length. The stretchable areas can allow for better and/or easier positioning of the small intestinal occlusion device 134 once introduced into the digestive system of the patient. Stretchable areas 104 can be made of a stretchable material (e.g., latex or rubber). In some cases the stretchable areas 104 can span the entire length of tubular body. In some embodiments, tubular body 134 has stretchable areas 104 that span at least about 5%, 10%, 25%, 50%, 75%, 80%, or 90% of its length. In some cases, the stretchable areas 104 of the tubular body 134 are made of a different material than the tubular body 138. For example, the stretchable areas 104 may be composed of a material that is more stretchable or pliable than the material of the rest of the tubular body 138. In some embodiments, the stretchable areas 104 are composed of the same material as the rest of the tubular body 138.

Figure 10:
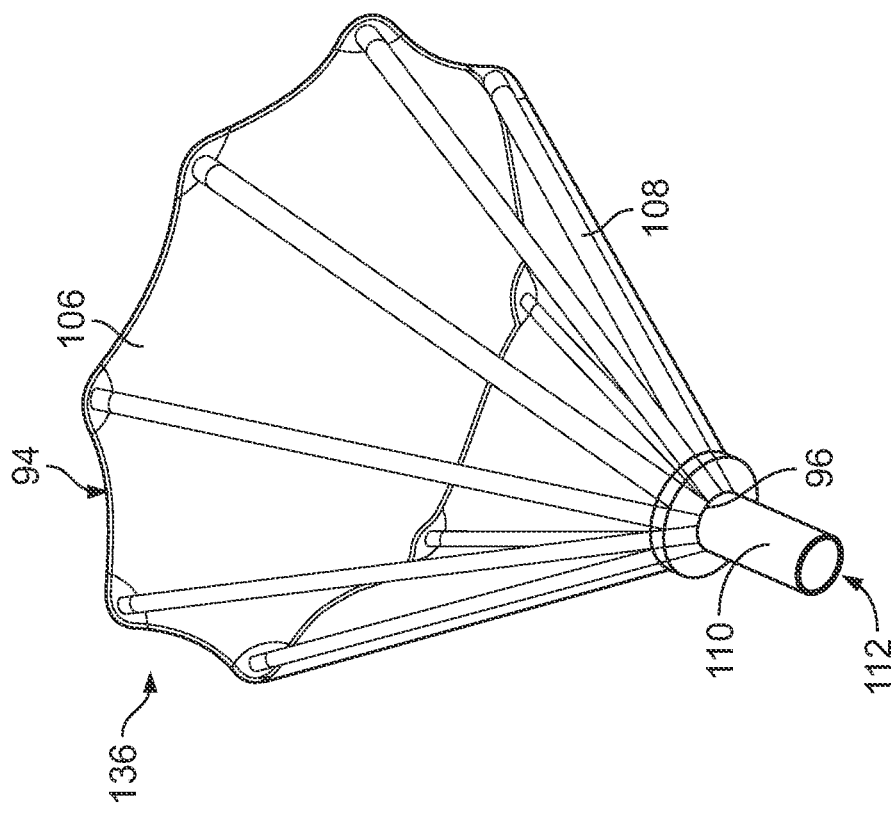
FIG. 10 is a side, perspective view of the occlusion member of the example small intestinal occlusion device of FIG. 7, in accordance with some embodiments provided herein.

Referring to FIG. 10, occlusion member 136 has a substantially conical shape that is formed by webbing 106 reinforced by multiple wires 108 that enable the occlusion member 136 to be reversibly expandable. In other words, the matrix of wires 108 allows the occlusion member 136 to collapse and expand in a similar manner as an umbrella. The reversibly expandable design allows the occlusion member 136 to be delivered in a contracted state via the mouth of the patient. Webbing 106 can be made of a pliable material (e.g., latex or silicone). Wires 108 are generally equally spaced apart from each other at the base 94 while stemming from the neck 96 of the occlusion member 136. In some cases, wires 108 are metal wires (e.g., nitinol wires). Occlusion member defines an opening (not shown in the figures) through which the tubular body 138 is received. Occlusion member 136 further includes a sleeve 110 at the neck 96 of the occlusion member 136. Sleeve 110 defines an opening 112 that is aligned with the opening of the occlusion member 136 and through which tubular body 138 is also received. In some cases, sleeve 110 is a weld that joins the occlusion member 136 with the tubular body 138. For example, occlusion member 136 can be welded to the outer surface of tubular body 138 in order to prevent sliding or movement of the tubular body 138 with respect to or through sleeve 110. In some embodiments, sleeve 110 and tubular body 138 can be crimped in order to prevent sliding or movement of the tubular body 138 with respect to or through sleeve 110. In some cases, sleeve 110 is a metal sleeve (e.g., a gold sleeve).

Figure 11:
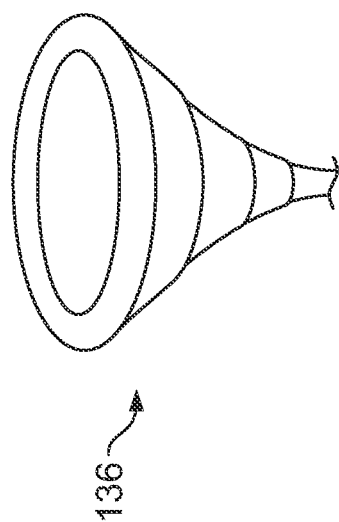
FIG. 11 is a side view of the occlusion member of the example small intestinal occlusion device of FIG. 7, in accordance with some embodiments provided herein.

FIG. 11 shows a side, perspective view of occlusion member 136. Occlusion member 136 can have a diameter of about 55 millimeters (mm) and a length of about 30 mm in an expanded state, as shown in FIGS. 10-11. In some cases, occlusion member 136 can have a diameter of about 25 mm to about 85 mm in an expanded state. In some cases, occlusion member 136 can have a length of about 10 mm to about 50 mm in an expanded state. Occlusion member 136 can have a diameter of about 15 millimeters (mm) and a length of about 35 mm in a contracted state (e.g., at the time of delivery of the device). In some cases, occlusion member 136 can have a diameter of about 10 mm to about 20 mm in a contracted state. In some cases, occlusion member 136 can have a length of about 10 mm to about 50 mm in a contracted state. Occlusion member has a strength (e.g., crush resistance or pressure resistance) of about 55 millimeters of mercury (mmHg).

Figure 12:
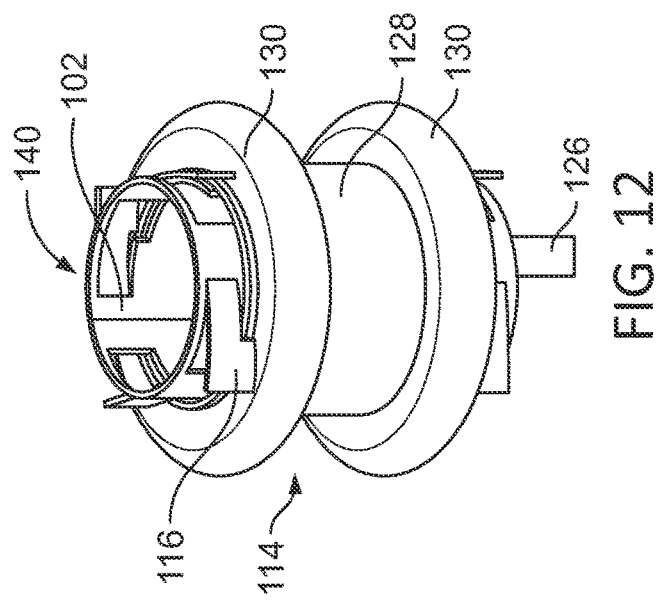
FIG. 12 is a side, perspective view of the anchor member of the example small intestinal occlusion device of FIG. 7, in accordance with some embodiments provided herein.

Referring to FIG. 12, anchor member 140 includes an outer sleeve 114 and a flexible sheet 102. Outer sleeve 114 has a cylindrical body 128 and a pair of flanges 130 extending from opposite ends of body 128. When the small intestinal occlusion device 134 is deployed into the digestive system of the patient, flanges 130 can ensure a tight seal between the stomach and the jejunum at the site of anastomosis. Cylindrical body 128 defines a lumen through which the flexible sheet 102 is received.

Figure 14:
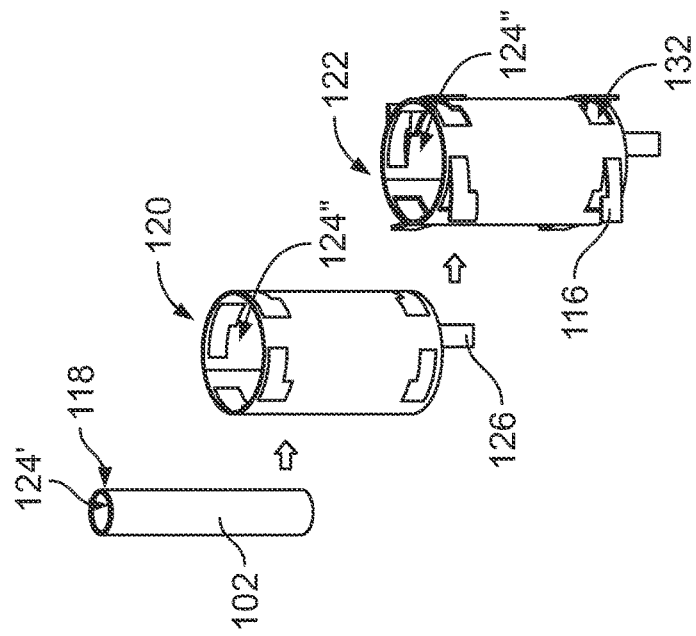
FIG. 14 is a side, perspective view of a flexible sheet of the anchor member of FIG. 12 in contracted and expanded positions, in accordance with some embodiments provided herein.
Figure 13:
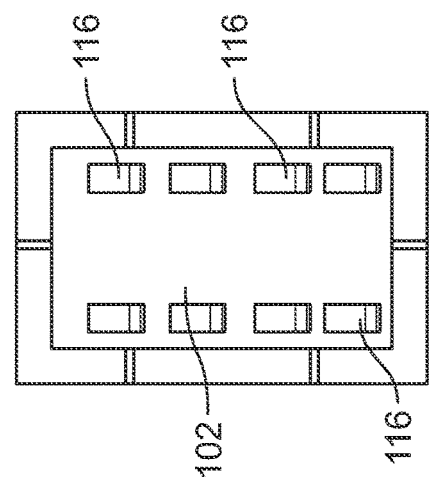
FIG. 13 is a front view of the flexible sheet of the anchor member of FIG. 11 in a flat position, in accordance with some embodiments provided herein.

Referring to FIG. 13, flexible sheet 102 is a rectangular sheet including multiple arms 116 located along the side edges of flexible sheet 102. Arms 116 are formed from perforated, rectangular sections of the flexible sheet 102. Flexible sheet 102 can be dynamically deployed from a generally flat state, as shown in FIG. 13, into a coiled state, as shown in FIG. 14. The flexible sheet 102 can be constricted or rolled into a cylindrical shape or stent in first position 118 where it is in a coiled state; for example, during insertion of the small intestinal occlusion device 78 (e.g., through the mouth of a patient). Flexible sheet 102 defines a first lumen 124' when rolled from a rectangular shape into a cylindrical shape. Upon release of an external pressure, flexible sheet 102 self-deploys into a wider cylindrical shape defining a second lumen 124" in second position 120. Second lumen 124" is greater than first lumen 124', as shown in FIG. 14. Flexible sheet 102 includes an attachment arm 126 that attaches the anchor member 140 to the bypass device 70. In a third position 122, the arms 116 of flexible sheet 102 self-deploy and interconnect with the multiple perforations 132 in order to lock the flexible sheet 102 into a fixed position to prevent movement and/or migration of the occlusion member 140. Lumen 124" can be located in the stomach, jejunum, duodenum, or a combination thereof (e.g., at an anastomosis site). In some cases, lumen 124" can align with an internal lumen of the liner 76. In some cases, lumen 124" can align with an internal lumen of the jejunum. In some cases, lumen 124" can align with an internal lumen of the duodenum. In some cases, lumen 124" can align with a diameter of the anastomosis.

Anchor member 140 can have a diameter of about 20 millimeters (mm) across flanges 130 in an expanded state, as shown in second position 120 and third position 122. In some cases, anchor member 140 can have a diameter of about 10 mm to about 30 mm in an expanded state. In some cases, anchor member 140 can have a length of about 20 mm in an expanded state. In some cases, anchor member 140 can have a length of about 10 mm to about 30 mm in an expanded state. In some cases, anchor member 140 can have a diameter of about 5 mm in a contracted or rolled state, as shown in first position 118. In some cases, anchor member 140 can have a diameter of about 5 mm to about 15 mm in a contracted or rolled state. In some cases, anchor member 140 can have an attachment strength of about 5 Newton (N) or about 1.12 pounds once deployed.

In some cases, the anchor member 140 can be an expandable disk or an expandable cone defining a lumen to anchor on an anastomosis. In some cases, the anchor member 140 can be a stent extending across the anastomosis. In some cases, the small intestinal occlusion device 134 is connected with the anchor member 140 via an expandable tubing, an expandable coil, or an expandable stent. In some cases, the occlusion member 140 is additionally connected to the small intestinal occlusion device 134 using hooks or an expandable coil on the gastric side of the apparatus to prevent migration and/or movement of the occlusion member 140 or the small intestinal occlusion device 134.

While this specification contains many specific implementation details, these should not be construed as limitations on the scope of any method or device or of what may be claimed, but rather as descriptions of features that may be specific to particular embodiments of particular methods and devices. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A system for bypassing a portion of a small intestine, the system comprising:
   an occlusion device comprising:
      a tubular member having a proximal end and a distal end, the tubular member configured to extend from the proximal end at an anastomosis between a stomach and the small intestine to the distal end at a first portion of the small intestine proximal to the stomach;
      an occlusion member connected to a distal end portion of the tubular member and configured to occlude a pyloric sphincter; and
      a first anchor member connected to the proximal end of the tubular member, such that a lumen of the first anchor member aligns with a lumen of the tubular member, the first anchor member configured to anchor the occlusion device in the anastomosis; and
   a bypass device configured to extend from the anastomosis through a second portion of the small intestine, the bypass device comprising:
      a liner configured to extend from the anastomosis through a portion of a jejunum; and
      a second anchor member at a proximal end portion of the liner and configured to engage with the first anchor member,
   wherein the occlusion device and the bypass device are deployable individually,
   wherein the bypass device is configured to be secured to the occlusion device by securing the second anchor member to the first anchor member in situ, and
   wherein the tubular member defines an aperture on a side of a body of the tubular member adjacent to the first anchor member, the aperture configured to: i) align with and provide access to the jejunum at the anastomosis, and ii) allow passage of the bypass device.

2. The system of claim 1, wherein the occlusion member is an inflatable balloon.

3. The system of claim 2, wherein the occlusion device comprises an inflation line communicably coupled to the inflatable balloon.

4. The system of claim 3, wherein the inflation line is removably coupled to the occlusion device.

5. The system of claim 1, wherein the occlusion member is a bumper.

6. The system of claim 5, wherein the bumper comprises a soft pliable material.

7. The system of claim 1, wherein the first anchor member has a conical shape.

8. The system of claim 1, wherein the tubular member is tapered.

9. The system of claim 1, wherein the tubular member is flexible.

10. The system of claim 1, wherein the liner is made of a flexible material.

11. The system of claim 10, wherein the liner has a length of about 40 cm to about 100 cm.

12. The system of claim 1, wherein the second anchor member has a conical shape.

13. The system of claim 1, wherein a distal tip of the tubular member is occluded and is configured to be positioned at the first portion of the small intestine proximal to the stomach.

14. The system of claim 13, further comprising a removable delivery loop extending from the distal tip of the tubular member.

* * * * *